United States Patent [19]

Köhne et al.

[11] Patent Number: 4,894,235

[45] Date of Patent: Jan. 16, 1990

[54] NIFEDIPINE-CONTAINING FORM OF ADMINISTRATION AND METHOD FOR ITS PRODUCTION

[75] Inventors: Hans Köhne, Obersulmetingen; Wolfgang Lahr, Laupheim; Hein U. Schmersahl, Ehingen-Gamerschwang, all of Fed. Rep. of Germany

[73] Assignee: Dr. Rentschler, Arzneimmittel GmbH & Co., Laupheim, Fed. Rep. of Germany

[21] Appl. No.: 783,862

[22] Filed: Oct. 3, 1985

[30] Foreign Application Priority Data

Oct. 23, 1984 [DE] Fed. Rep. of Germany ....... 3438830

[51] Int. Cl.$^4$ .......................... A61K 9/48; A61K 9/66
[52] U.S. Cl. ...................... 424/452; 424/78; 424/455; 514/962
[58] Field of Search .............. 514/356, 962; 424/78, 424/80, 452, 455, 457, 465, 468, 482, 486, 497, 502, 452, 455, 78

[56] References Cited

U.S. PATENT DOCUMENTS

| | | | |
|---|---|---|---|
| 3,139,383 | 6/1964 | Neville | 424/462 |
| 3,297,804 | 1/1967 | Iwamoto et al. | 424/458 |
| 3,374,146 | 3/1968 | Bucharz et al. | 424/457 |
| 3,784,684 | 1/1974 | Bassert et al. | 424/455 |
| 3,862,311 | 1/1975 | Leeson | 424/78 |
| 4,151,273 | 4/1979 | Riegelman et al. | 424/78 |
| 4,343,789 | 8/1982 | Kawata et al. | 424/497 |
| 4,404,183 | 9/1983 | Kawata et al. | 424/499 |
| 4,412,986 | 11/1983 | Kawata et al. | 424/80 |
| 4,454,152 | 6/1984 | Barry et al. | 514/455 |
| 4,497,158 | 2/1985 | Durr et al. | 424/452 |
| 4,562,069 | 12/1985 | Hegasy et al. | 424/80 |
| 4,665,081 | 5/1987 | Doi et al. | 514/356 |

OTHER PUBLICATIONS

Kaken C.A. 95:225681J (1981) of Jpn. KT.K. 81, 115,726, Sep. 11, 1981, Nifedipine Formulations containing Polyethylene Glycol.

*Primary Examiner*—Shep K. Rose
*Attorney, Agent, or Firm*—James W. Hellwege

[57] ABSTRACT

An improved form of administration of 1,4-dihydro-2,6-dimethyl-4-(2-nitrophenyl)-3,5-pyridine-dicarboxylic acid-dimethylester (i.e., Nifedipine) is provided in which the Nifedipine is molecularly dispersed wihtin a solidified melt of polyethylene glycols which are liquid, semi-solid and solid at room temperature. The weight ratio of liquid to non-liquid polyethylene glycols in the solidified melt ranges from about 7:23 to 23:7, the solidification temperature of the mixture ranges from about 25° C. to 62° C. and the mixture has a viscosity of from about 1 to 180,000 poise when measured at 20° C. in admixture with up to about 40 percent by weight of water.

22 Claims, 3 Drawing Sheets

NIFEDIPINE-CONTAINING FORM OF ADMINISTRATION AND METHOD FOR ITS PRODUCTION

BACKGROUND OF THE PRESENT INVENTION

This invention relates to a new 1,4-dihydro-2,6-dimethyl-4(2-nitrophenyl)-3,5-pyridine-dicarboxylic acid-dimet (Nifedipine)-containing form of administration, in which the Nifedipine is molecularly dispersed within a solidified melt of various polyethylene glycols. The mixture containing the effective substance ranges from very viscous to solid at room temperature and is accordingly incapable of independent flow at room temperature. The mixture is placed as a melt into hard gelatin capsules and the cooled to room temperature to provide a suitable means of administration.

The effective substance 1,4-dihydro-2,6-dimethyl-4-(2-nitrophenyl)-3,5-pyridine-dicarboxylic acid-dimethylester (Nifedipine) belongs to the group of calcium antagonists and has attained great importance because of its pronounced antianginal, antiarythmic, anti-hypertensive and cardioprotective effect for the long-term therapy of coronary heart diseases, especially in the case of life threatening critical high blood pressure.

It is known from DE-OS 22 095 26 that gelatin bite capsules (soft gelatin capsules) may be filled with a mixture of one part by weight Nifedipine, 650 parts by weight polyalkylene glycols with an average molecular weight of 200 to 4000, 1 to 10 parts by weight lower alcohols and further formulation aids, with these soft gelatin capsules further containing an opaquing means e.g., a dyestuff) which absorbs light of the wavelength 250 nm–460 nm.

This known form of administration, and in particular the method for its production, suffers from the disadvantage that the capsule production and filling must be carried out in one step, for which special knowledge is required in addition to a major expense in the form of special production machines. Therefore, naturally, the soft gelatin capsules are one of the most expensive forms of administration. A further drawback is that the soft gelatin capsules have to be filled in a manner such that they are practically air-free so that their mechanical stability is ensured. It follows that the filling volume or weight of a capsule cannot be varied as that would require different capsule sizes as well as differing expensive packaging tools.

Use of the known soft gelatin capsules also necessitates that the filling material meet special requirements due to the composition of the capsule material and the fact that the capsule constitutes a completely closed unit. It must be absolutely avoided during production that protein-precipitating substances enter the capsule interior together with the filling goods because they cause the gelatin to form high molecular weight water insoluble products. After hardening the soft gelatin capsule thus dissolves with difficulty in the digestive tract, or not at all, so that the medicament is released for resorption only after much delay or not at all.

Aldehydes are known protein-precipitating substances. Polyalkylene glycols, however, during decay form aldehydes (among other products) (Company brochure of the firm Hoechst Ag, "Polyglycols Hoechst" 1981). As such, special attention must be paid to the use of aldehyde-free polyethylene glycols when filling soft gelatin capsules. Polyethylene glycols having an aldehyde content of more than 5 ppm can therefore not be used for the production of such soft gelatin capsules in order to ensure that the capsule can dissolve satisfactorily in the digestive tract. This is considered to be a significant drawback regarding this known form of administration.

OBJECTS AND SUMMARY OF THE PRESENT INVENTION

The object of the present invention is thus to provide a Nifedipine-containing form of administration which quickly releases the effective substance contained therein and thereby creates rapidly increasing, therapeutically effective blood levels thereof, which can be produced without great expense and in spite of the presence of polyethylene glycols is not accompanied by the risk of not dissolving and thus not releasing the effective substance.

This object is attained according to the invention by working the Nifedipine into a mixture of different polyethylene glycols in the melt (as herein defined), and filling this melt about 10° C. above its solidification point into the lower portion of hard gelatin capsules, closing the lower portion of the capsule with the upper portion of the capsule and thus obtaining the finished form of administration.

In accordance with the present invention there is thus provided an administratable composition comprised of Nifedipine molecularly dispersed within a solidified melt comprised of a mixture of polyethylene glycols selected from the group consisting of polyethylene glycols which are liquid, semi-solid and solid at room temperature, the weight ratio of liquid to non-liquid polyethylene glycols in said solidified melt ranging from about 7:23 to 23:7, the solidification temperature of the mixture ranging from about 25° C. to 62° C. and the mixture having a viscosity ranging from about 1 to 180,000 poise when measured at 20° C. in admixture with up to about 40 percent by weight of water.

In accordance with the present invention there is also provided an administratable composition in the form of a hard gelatin capsule containing an effective amount of Nifedipine molecularly dispersed within a solidified melt comprised of a mixture of polyethylene glycols selected from the group consisting of polyethylene glycols which are liquid, semi-solid and solid at room temperature, the weight ratio of liquid to non-liquid polyethylene glycols in said solidified melt ranging from about 7:23 to 23:7, the solidification temperature of the mixture ranging from about 25° C. to 62° C. and the mixture having a viscosity ranging from about 1 to 180,000 poise when measured at 20° C. in admixture with up to about 40 percent by weight of water.

In accordance with the present invention there is further provided a method of administering an effective amount of Nifedipine to a patient to effect treatment of a Nifedipine-treatable condition, the improvement comprising administering to said patient said effective amount of Nifedipine molecularly dispersed within a solidified melt comprised of a mixture of polyethylene glycols selected from the group consisting of polyethylene glycols which are liquid, semi-solid and solid at room temperature, the weight ratio of liquid to non-liquid polyethylene glycols in said solidified melt ranging from about 7:23 to 23:7, the solidification temperature of the mixture ranging from about 25° C. to 62° C. and the mixture having a viscosity ranging from about 1 to 180,000 poise when measured at 20° C. in admixture with up to about 40 percent by weight of water.

In accordance with the present invention there is still further provided a method of production of Nifedipine-containing hard gelatin capsules suitable for administration to a patient comprising the steps of (1) providing a melt comprised of a mixture of polyethylene glycols which are liquid, semi-solid and solid at room temperature in which Nifedipine is dissolved, the weight ratio of liquid to non-liquid polyethylene glycols in said melt ranging from about 7:23 to 23:7, the solidification temperature of the mixture ranging from about 25° C. to 62° C. and the mixture having a viscosity ranging from about 1 to 180,000 poise when measured at 20° C. in admixture with up to about 40 percent by weight of water and (2) filling at least a portion of a hard gelatin capsule with said melt, the melt being at a temperature of at least about 10° C. above the solidification temperature of the melt when added to said capsule.

DETAILED DESCRIPTION OF THE INVENTION

Figure 1:
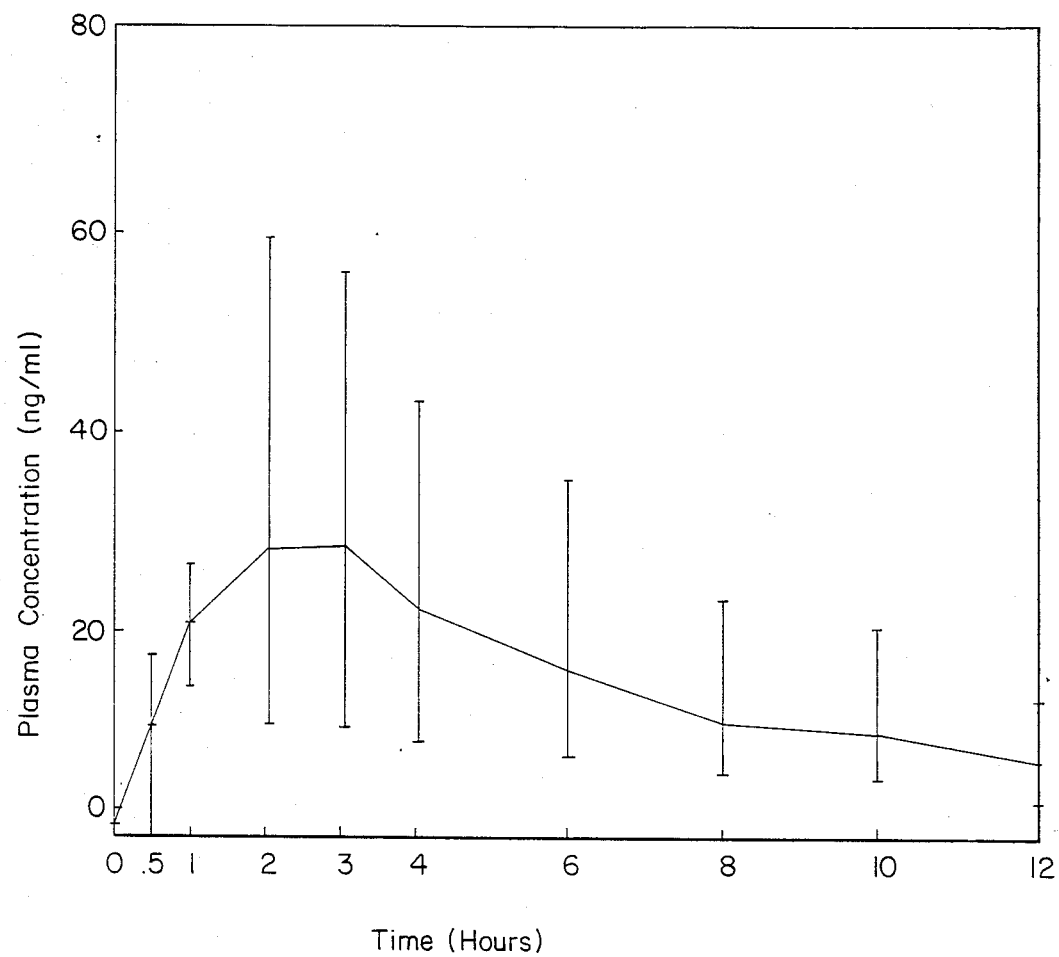
FIGS. 1-3 graphically depict the bioavailability rate of Nifedipine as a result of the administration of same by tablet, solution and according to the present invention, respectively.

Hard gelatin capsules have the decisive advantage in that they are commercially available and can thus be arbitrarily filled with conventional capsule-filling machines that are suitable for liquid filling, whereby the filling amount may be varied and is limited by the volume of the lower body of the capsule. Hard gelatin capsules further have the advantage of consisting of two parts that are slid into one another after filling. Thus no hermetical closure of the capsule parts is necessary.

In any case, digestive liquids can penetrate the interior of the capsule even then when the goods which fill the capsule include protein-precipitating substances which can cause undesirable lattice-like polymerization of the gelatin.

Nifedipine is a substance which is practically insoluble in water. Its solubility in low molecular weight, liquid polyethylene glycols is very good, however. In higher molecular weight semisolid and solid polyethylene glycols the Nifedipine can be dissolved in the melt, with the Nifedipine crystallizing after cooling to room temperature in the solidified polyethylene glycol. For quick resorption within the digestive tract, the Nifedipine must, however, be fed to the organism in dissolved form, whereby the rate of solution of the Nifedipine is the factor determining the resorption rate. Liquid low molecular weight polyethylene glycols cannot be used to fill hard gelatin capsules without the addition of thickening substances. The danger of leakage exists which can only be countered by a large additional technical expense by sealing the capsule halves (e.g. by taping glueing). Thickening substances can, however, serve as seed crystals and cause the dissolved Nifedipine to recrystallize out of the polyethylene glycol mass.

It has been surprisingly and unexpectedly discovered that by using mixtures of liquid, semi-solid and solid polyethylene glycols in specified ratios, compositions which lend themselves to filling are obtained in which the Nifedipine is molecularly dispersed, but which solidifies or become so viscous after cooling to room temperature that the substance will no longer leak out of the hard gelatin capsule and the Nifedipine will accordingly not recrystallize.

It is essential according to the present invention for the composition of the fillable substances that both liquid and non-liquid (i.e., semi-solid and solid) polyethylene glycols be used in the sense of the preceding definition in a weight ratio of from about 7:23 to 23:7, preferably from about 12:7 to 20:12, which are characterized by a solidification point between about 25° C. and 62° C., preferably between about 35° C. to 45° C.

The term "liquid" polyethylene glycols is intended to include those of molecular weights from about 200 to about 600, "semi-solid" is intended to include those with mean molecular weights from about 600 to about 1500 and "solid" polyethylene glycols is intended to include such with mean molecular weights above about 1500 (Catalog of Pharmaceutical Adjuvants, Sales Department of the Working Group of Pharmaceutical Industrial Processing Engineering, 1974).

A further characteristic of the composition of the polyethylene glycol mixtures used according to the invention is their viscosity (measured with Brookfield rotary viscosimeter, type RVT). Because the mixtures should not be capable of independent flow at room temperature, it is not practical to measure their viscosity at room temperature. Therefore, mixtures are usefully produced with up to about 40 percent by weight of demineralized water and polyethylene glycol mixtures, tempered to 20° C. and measured with the aforesaid device. Polyethylene glycol mixtures suitable for use according to the present invention consequently possess viscosities of about 1 Poise up to about 180,000 Poise when measured under such conditions.

Thus, for example, a mixture of polyethylene glycols with mean molecular weights of 200 and 2000 in the weight ratio of 22:8, respectively, exhibit a viscosity as an 80 percent by weight aqueous solution of 5.66 Poise and a mixture of polyethylene glycols with mean molecular weights of 200 and 35,000 in the weight ratio of 8:22, respectively, as a 60 percent by weight aqueous solution exhibits a viscosity of 172,000 Poise.

In the polyethylene glycol mixtures characterized by the mixing ratios, the solidification range and the viscosity, the effective substance Nifedipine is preferably added in such a manner that it is first dissolved under stirring at room temperature in the liquid polyethylene glycol component. Subsequently, the non-liquid portion of polyethylene glycol is added and the mixture is heated until a clear melt has formed which is added to the hard gelatin capsules at a temperature about 10° C. above the solidification point of the mixture.

The content of Nifedipine in the melt generally ranges between about 1 and 10 percent by weight, preferably between about 3 and 7 percent by weight, based on the weight of the total composition. Furthermore, solubilizing and/or viscosity increasing adjuvants can be added to the melt, such as e.g., polyvinylpyrrolidone and/or highly dispersive silicic acid, whereby the choice has to be made in such a way that these adjuvants do not promote recrystallization of the Nifedipine. Of course, other adjuvants can be used, for example, substances which protect the per se very photo-sensitive substance Nifedipine from decay due to the influence of light, such as e.g., the dyestuff "yellow orange S". Such additions must not, of course, promote a recrystallization of the effective substance.

The filling weight of the gelatin hard capsule depends upon the concentration of the effective substance in the melt and the desired dosage to be administered. The size of the hard gelatin capsule also depends upon the concentration of the effective substance in the melt and the desired dose in the form of administration. Capsules of a volume of about 0.68 ml to 0.21 ml, in particular of a volume of about 0.68 ml to 0.30 ml, such as e.g., conventional hard gelatin capsules of size Zero, One, Two or Three are preferred. The content of Nifedipine per capsule generally amounts to about 5 to 20 mg, in particular about 10 mg.

The production of mixtures containing effective substance is preferably carried out by dissolving Nifedipine in the total absence of light into low molecular weight, liquid polyethylene glycol at room temperature. If required, a suitable adjuvant, such as e.g., the dyestuff "yellow orange S" is also stirred in as protecting against light. After adding the necessary non-liquid polyethylene glycols, the mixture is heated under stirring, until a clear melt is attained. If necessary, viscosity increasing and/or solubilizing adjuvants are now stirred in. The mixture is cooled to about 10° C. above its solidification point and filled into the capsules.

It has now been surprisingly demonstrated that the effective substance Nifedipine in the form of administration according to the present invention is preserved over long periods of time in molecularly dispersed form. Contrary to expectation, the effective substance is released either to a large degree or completely from the form of administration in an artificial release model according to JS Pharmacopeia XX p. 959 within 30 It would have been expected that the Nifedipine would recrystallize immediately upon contact with the aqueous release medium thus becoming practically insoluble.

While in vitro tests alone do not indicate the extent of the availability of the effective substance in the human organism, the formulation of Example 6 of the invention was tested for bio-availability on ten healthy test persons. For comparison, a true solution of Nifedipine in pure, liquid polyethylene glycol with a mean molecular weight of 200 as well as a conventional tablet, in which the Nifedipine was present in crystalline form, were used.

The Nifedipine dose administered in the form according to the present invention and the solution amounted in each case to 10 mg and for the tablet 20 mg. The dose for the tablet was chosen to be double the amount for the other two to ensure that plasma concentrations could be measured with sufficient accuracy, because a lesser bio-availability was to be expected with increasing plasma concentrations due to the lessened solubility of the Nifedipine.

Figure 2:
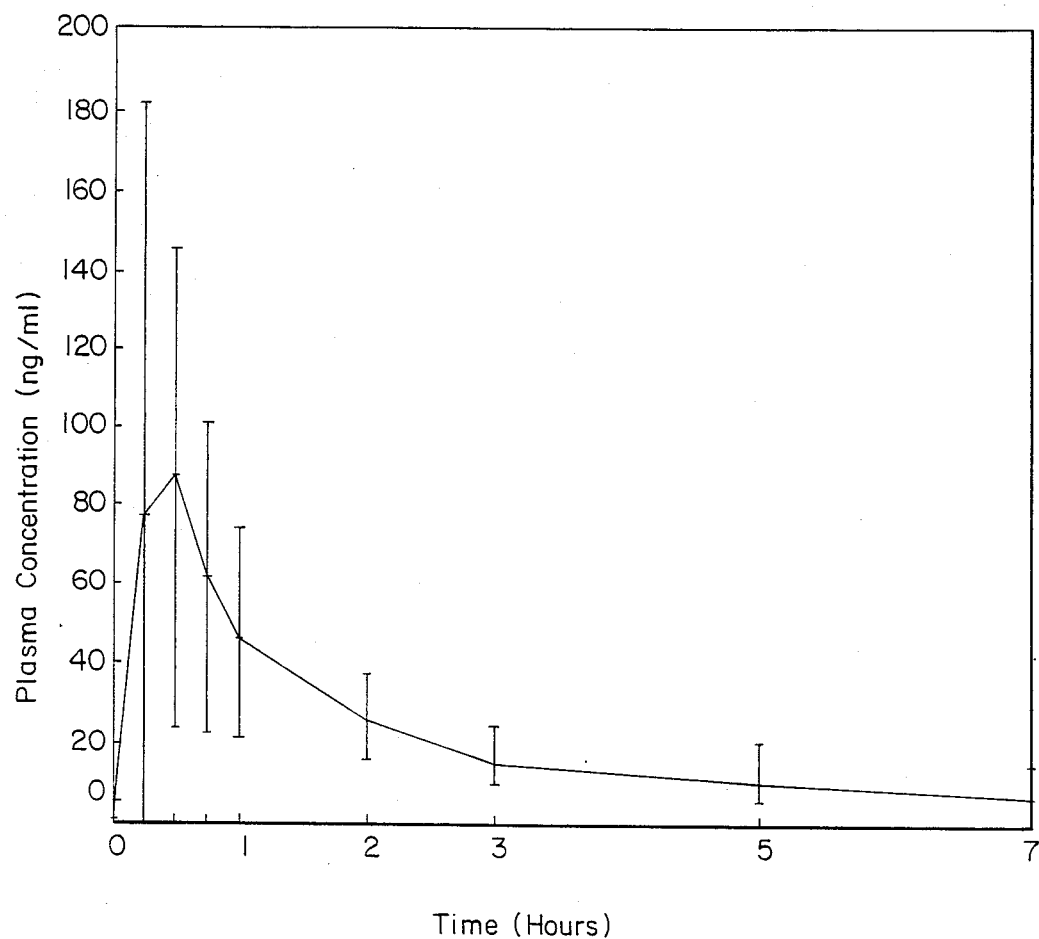
Figure 3:
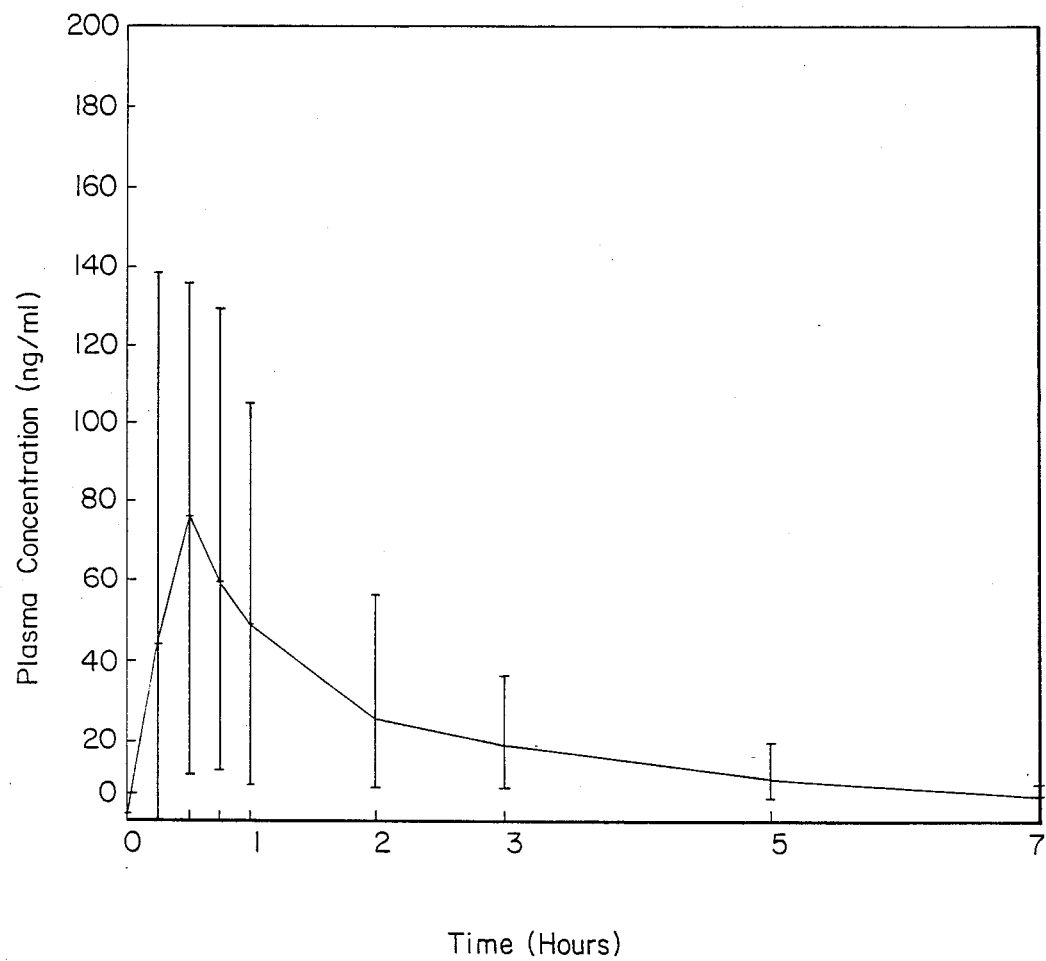

The solution was chosen as a direct comparison to the form according to the present invention because it was to be expected that with this form the best bio-availability with respect to a solid drug form was achievable. The superiority of true solutions over other forms of medicine with respect to the biological availability is shown, for example, by Ritschel, Applied Biopharmacy, Stuttgart 1973, p. 346–347. The results of these investigations are shown in FIGS. 1–3 and summarized in Table 1 below:

TABLE 1

| Biovailability of Nifedipine | | | | | |
|---|---|---|---|---|---|
| Tablet Form | | Solution Form | | Present Invention | |
| Individual Values (Hrs) | Concentration (ng/ml) | Individual Values (Hrs) | Concentration ng/ml | Individual Values (Hrs) | Concentration (ng/ml) |
| 0.0 | 1.1 | 0.0 | 1.3 | 0.0 | 2.0 |
| 0.5 | 11.1 | 0.25 | 76.9 | 0.25 | 44.2 |
| 1.0 | 20.8 | 0.50 | 87.7 | 0.50 | 75.8 |
| 2.0 | 29.3 | 0.75 | 61.4 | 0.75 | 59.5 |
| 3.0 | 29.7 | 1.0 | 46.4 | 1.0 | 48.9 |
| 4.0 | 22.0 | 2.0 | 25.1 | 2.0 | 25.4 |
| 6.0 | 18.0 | 3.0 | 14.3 | 3.0 | 18.7 |
| 8.0 | 10.9 | 5.0 | 9.2 | 5.0 | 10.1 |
| 10.0 | 9.8 | 7.0 | 5.8 | 7.0 | 8.2 |
| 12.0 | 7.1 | — | — | — | — |

Tablet Form: 1 tablet dosage, 20 mg. per tablet
Solution Form: 1 ml dosage, 10 mg. per ml solution
Present Invention: 1 capsule dosage, 10 mg. per capsule FIG. 1 and Table 1 show the trend of the plasma concentration of the Nifedpine from the conventional tablet with time. As expected, the increase in the plasma concentration is slow because of the lower solution rate of Nifedipine in aqueous systems, the maximum plasma concentration being attained after about 2 hours. The curve shows that the crystalline effective substance acts self-retarding.

FIG. 2 and Table 1 show the expected trend with time of the plasma concentration of Nifedipine from the solution, whereby the plasma concentration increases to a maximum value after only 30 minutes which can be explained by the fact that contrary to Example 1 the step determining resorption, namely the solution rate of the effective substance, falls away.

Surprising, however, are the results of FIG. 3 which show that from the form according to the present invention high plasma concentrations of Nifedipine can be reached nearly as rapidly as in the comparison of FIG. 2; in particular, when considering that for Nifedipine the lower limit for blood plasma levels amounts to 10 to 15 nanograms per milliliter (Ramsch, Selecta 10, p. 860, of Mar. 7, 1983), even though the form of administration has to first be dissolved with the solidified melt. The determining step for the resorption and the resorption rate, the solution rate of the capsule contents, evidently does not impede the extent of absorption.

Furthermore, if one compares the areas under the plasma concentration time curve, AUC (Area under the curve) which usually serve as a measure of the bio-availability, it becomes surprisingly clear that the form according to the invention is 100 percent bio-equivalent with respect to the following comparison:

| | |
|---|---|
| AUC for form according to invention (FIG. 3) | 154 ng hr/ml |
| AUC for comparison (FIG. 2) | 154 ng hr/ml |

Rather one would have expected that the Nifedipine would partially recrystallize in the digestive tract during the solution phase, which should have led to a reduced bio-availability with respect to the comparison.

Therefore, consistent with the aforementioned object of the present invention a form of administration for Nifedipine is provided that can h=produced with economic advantage compared to the state of the art, with commercially available tools, which is insensitive to the disadvantageous gelatin hardening due to aldehyde separation from polyethylene glycols, which offers a large margin in the dosage per capsule size, provides a precise dosage of the effective substance and because of the complete release of the effective substance from the form of administration possesses the same therapeutical advantage as individual dose in the form of a true solution, whereby the rapid surging of the effective substance in therapeutically effective concentrations in the blood plasma also makes this form especially suitable for the treatment of critical high blood pressure.

The invention is further described in Examples 1 to 10 of the following Table 2 in more detail:

TABLE 2

| | Example | | | | | | | | | |
|---|---|---|---|---|---|---|---|---|---|---|
| | 1 | 2 | 3 | 4 | 5 | 6 | 7 | 8 | 9 | 10 |
| | Composition (Parts by weight) | | | | | | | | | |
| Nifedipine | 5 | 5 | 5 | 5 | 5 | 5 | 5 | 10 | 5 | 5 |
| Polyethylene glycol Mean mol. weight 200 | 70 | 100 | 80 | 100 | 80 | 60 | 90 | 110 | 35 | 80 |
| Polyethylene glycol Mean mol. weight 2000 | 80 | — | — | — | — | — | — | — | — | — |
| Polyethylene glycol Mean mol. weight 6000 | — | 50 | — | — | — | 35 | 55 | 40 | 115 | 65 |
| Polyethylene glycol Mean mol. weight 10,000 | — | — | 70 | — | — | — | — | — | — | — |
| Polyethylene glycol Mean mol. weight 20,000 | — | — | — | 50 | — | — | — | — | — | — |
| Polyethylene glycol Mean mol. weight 35,000 | — | — | — | — | 70 | — | — | — | — | — |
| Polyvinylpyrrolidone (KOLLIDON 25) | — | — | — | — | — | 5 | 4 | — | — | 5 |
| Yellow Orange S | — | — | — | — | — | — | 1 | — | — | — |
| Ratio | | | | | | | | | | |
| Liquid PEG: Non-liquid PEG | 14:16 | 20:10 | 16:14 | 20:10 | 16:14 | 12:7 | 18:11 | 22:8 | 7:23 | 16:13 |
| Content Nifedipine in the melt (% by weight) | 3.2 | 3.2 | 3.2 | 3.2 | 3.2 | 4.76 | 3.2 | 6.25 | 3.2 | 3.2 |
| Viscosity (Poise) | | | | | | | | | | |
| 80% mixture 20% water | 783 | — | — | — | — | — | — | 1.234 | — | — |
| 60% mixture 40% water | — | 6,600 | 5.4 | 6.7 | 988 | 1.7 | 2.1 | — | 6.1 | 2.7 |
| Solidification point Approx. °C. | 34.5 | 38.0 | 40.0 | 40.0 | 43.5 | 36.5 | 37.5 | 37.5 | 41.0 | 37.5 |
| Capsule volume (ml) or capsule size, respectively | 0.3 / 3 | 0.3 / 3 | 0.3 / 3 | 0.3 / 3 | 0.3 / 3 | 0.3 / 3 | 0.68 / 0 | 0.5 / 1 | 0.3 / 3 | 0.3 / 3 |
| mg Nifedipine/capsules | 10 | 10 | 10 | 10 | 10 | 10 | 20 | 20 | 5 | 10 |
| in vitro release in % (in 30 minutes) | 87.9 | 87.0 | 76.0 | 90.5 | 81.5 | 100 | 91.8 | 95.2 | 93.7 | 91.2 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. In an administratable composition in the form of a hard gelatin capsule containing an effective amount of Nifedipine molecularly dispersed within a solidified melt comprised of a mixture of liquid and non-liquid polyethylene glycols selected from the group consisting of polyethylene glycols which are liquid, semi-solid solid and solid at room temperature, the improvement wherein said liquid and non-liquid polyethylene glycols are present in said solidified melt in a weight ratio of liquid to non-liquid polyethylene glycols ranging from about 7:23 to 23:7, the solidification temperature of the mixture ranging from about 25° C. to 62° C. and the mixture having a viscosity ranging from about 1 to 180,000 poise when measured at 20° C. in admixture with up to about 40 percent by weight of water, whereby leakage of the polyethylene glycol melt upon solidification of same from said capsule is avoided and the molecularly dispersed Nifedipine will not recrystallize with said melt while avoiding decreased bioavailability of the Nifedipine due to the reduced solubility exhibited by the recrystallized Nifedipine.

2. The composition of claim 1 wherein said weight ratio of liquid to non-liquid polyethylene glycols ranges from about 12:7 to 20:12.

3. The composition of claim 1 wherein said Nifedipine is present in an amount ranging from about 1 to 10 percent by weight based on the total weight of the composition.

4. The composition of claim 3 wherein said Nifedipine is present in an amount ranging from about 3 to 7 percent by weight based on the total weight of the composition.

5. The composition of claim 1 wherein said solidification temperature ranges from about 35° to 45° C.

6. The composition of claim 1 further comprising an adjuvant selected from the group consisting of viscosity increasing adjuvants, solubilizing adjuvants, agents protecting against light, and mixtures thereof.

7. The composition of claim 6 wherein said adjuvant comprises the dyestuff yellow-orange S as an agent protecting against light.

8. The composition of claim 6 wherein said adjuvant comprises polyvinylpyrrolidone.

9. The composition of claim 6 wherein said adjuvant comprises silicic acid.

10. The composition of claim 1 wherein said capsule has a volume of from about 0.21 to 0.68 milliliters.

11. In a method of administering an effective amount of Nifedipine in a hard gelatin capsule to a patient to effect treatment of a Nifedipine-treatable condition, comprising administering to said patient said effective amount of Nifedipine molecularly dispersed within a solidified melt comprised of a mixture of liquid and non-liquid polyethylene glycols selected from the group consisting of polyethylene glycols which are liquid, semi-solid and solid at room temperature, the improvement wherein said liquid and non-liquid polyethylene glycols are present in said solidified melt in a weight ratio of liquid to non-liquid polyethylene glycols ranging from about 7:23 to 23:7, the solidification temperature of the mixture ranging from about 25° C. to 62° C. and the mixture having a viscosity ranging from about 1 to 180,000 poise when measured at 20° C. in admixture with up to about 40 percent by weight of water, whereby leakage of the polyethylene glycol melt upon solidification of same from the capsule is avoided and the molecularly dispersed Nifedipine will not recrystallize within said solidified melt while avoiding decreased bioavailability of the Nifedipine due to the reduced solubility exhibited by the recrystallized Nifedipine.

12. The method of claim 11 wherein said weight ratio of liquid to non-liquid polyethylene glycols ranges from about 12:7 to 20:12.

13. The method of claim 11 wherein said Nifedipine is present in an amount ranging from about 1 to 10 percent by weight based on the total weight of the composition.

14. The method of claim 13 wherein said Nifedipine is present in an amount ranging from about 3 to 7 percent by weight based on the total weight of the composition.

15. The method of claim 11 wherein said solidification temperature ranges from about 35° to 45° C.

16. The method of claim 11 further comprising an adjuvant selected from the group consisting of viscosity increasing adjuvants, solubilizing adjuvants, agents protecting against light, and mixtures thereof.

17. The method of claim 16 wherein said adjuvant comprises the dyestuff yellow-orange S as an agent protecting against light.

18. The method of claim 16 wherein said adjuvant comprises polyvinylpyrrolidone.

19. The method of claim 16 wherein said adjuvant comprises silicic acid.

20. The method of claim 11 wherein said solidified melt is administered in the form of a hard gelatin capsule.

21. The method of claim 20 wherein said capsule has a volume of from about 0.21 to 0.68 milliliters.

22. The composition of claim 1 wherein said capsule has a volume of from about 0.21 to 0.68 milliliters.

* * * * *